US008519227B2

(12) United States Patent
Tanaka et al.

(10) Patent No.: US 8,519,227 B2
(45) Date of Patent: Aug. 27, 2013

(54) ULTRA-FAST TRANSFORMATION TECHNIQUE FOR MONOCOTYLEDONS

(76) Inventors: Hiroshi Tanaka, Tsukuba (JP); Toshiaki Kayano, Tsukuba (JP); Masashi Ugaki, Tsukuba (JP); Fumio Shiobara, Tsukuba (JP); Naoto Shibuya, Tsukuba (JP); Haruko Onodera, Tsukuba (JP); Kazuko Ono, Tsukuba (JP); Akemi Tagiri, Tsukuba (JP); Yaeko Nishizawa, Tsukuba (JP)

( * ) Notice: Subject to any disclaimer, the term of this patent is extended or adjusted under 35 U.S.C. 154(b) by 555 days.

(21) Appl. No.: 10/979,542

(22) Filed: Nov. 2, 2004

(65) Prior Publication Data

US 2005/0138694 A1    Jun. 23, 2005

Related U.S. Application Data

(63) Continuation of application No. 09/914,546, filed on Mar. 12, 2002, now abandoned.

(51) Int. Cl.
*A01H 5/00* (2006.01)
*A01H 5/10* (2006.01)
*C12N 15/82* (2006.01)

(52) U.S. Cl.
USPC ............ 800/294; 435/469; 800/278; 800/284

(58) Field of Classification Search
USPC ................ 435/469, 419; 536/23.1; 800/278, 800/298, 294, 320.2, 320
See application file for complete search history.

(56) References Cited

U.S. PATENT DOCUMENTS 5,569,597 A    10/1996   Grimsley et al.

FOREIGN PATENT DOCUMENTS

EP            0 897 013 A1    2/1999

OTHER PUBLICATIONS

Birch, Annu. Rev. Plant Physiol. Plant Mol. Biol. 1997, 48:297-326 especially p. 302, and Figure 1, p. 304.*
Bowen, B. (Markers for plant gene transfer, vol. 1: 89-123, in Kung and Wu, eds, 1993, Transgenic Plants, vol. 1 and 2, SanDiego, Academic Press)).*
Toki, "Rapid and Efficient Agrobacterium mediated transformation in Rice", 1997, Plant Molecular Biology Reporter, vol. 15, No. 1, pp. 16-21.*
See attached: wikiiipedia.org printout Feb. 20, 2007 p. 3.*
Toki 1997 Plant Molecular Biology Reporter 15:16-21.*
Dale et al Plant Science 1989 63:237-245.*
Graves et al., *The transformation of Zea mays seedlings with Agrobacterium tumefaciens*, Plant Molecular Biology 7, pp. 43-50, 1986.
Bytebier et al., *T-DNA organization in tumor cultures and transgenic plants of the monocotyledon Asparagus officinalis*, Proc. Natl. Acad. Sci. USA, vol. 84, pp. 5345-5349, Aug. 1987, Genetics.
Schafer et al., *T-DNA integration and expression in a monocot crop plant after induction of Agrobacterium*, Department of Biology, Plant Molecular Biology Group, University of Frankfurt, Letters to Nature, Nature, vol. 327, pp. 529-532, Jun. 11, 1987.
Sommer et al., *Genetic engineering of shikonin biosynthesis hairy root cultures of Lithospermum erythrorhizon transformed with the bacterial ubiC gene*, Plant Molecular Biology 39, pp. 683-693, 1999.
Toki, *Rapid and Efficient Agrobacterium-Mediated Transformation in Rice*, Genetic Resources, Plant Molecular Biology Reporter, 15 (1) 1997, pp. 16-21.
McCormac et al., *The use of visual marker genes as cell-specific reporters of Agrobacterium-mediated T-DNA delivery to wheat (Triticum aestivum L.) and barley (Hordeum vulgare L.)*, Euphytica 99, pp. 17-25, 1998.
Kang et al., *Identification of class B and class C floral organi identity genes from rice plants*, Plant Molecular Biology 38, pp. 1021-1029, 1998.
Uze et al., *Plasmolysis of precultured immature embryos improves Agrobacterium mediated gene transfer to rice (Oryza sativa L.)*, Plant Science, 130 (1997), pp. 87-95.
Park et al., *T-DNA integration into genomic DNA of rice following Agrobacterium inoculation of isolated shoot apices*, Plant Molecular Biology, 32, pp. 1135-1148, 1996.
Sakamoto et al., *Metabolic engineering of rice leading to biosynthesis of glycinebetaine an dtolerance to salt and cold*, Plant Molecular Biology, 38, pp. 1011-1019, 1998.
Daigen et al., Hokuriku Sakumotsu-Gakkaiho, 30, pp. 80-82, 1995 (partial translation).
Yokoi et al., *Tapetum-specific expression of the OSG6B promoter-β-glucuronidase gene in transgenic rice*, Plant Cell Reports, 16, pp. 363-367, 1997.
Hiei et al., *Efficient transformation of rice (Oryza sativa L.) mediated by Agrobacterium and sequence analysis of the boundaries of the T-DNA*, The Plant Journal, 6(2), pp. 271-282, 1994.
Raineri et al., *Agrobacterium-mediated transformation of rice (Oryza sativa L.)*, Research Papers, Bio/Technology, vol. 8, pp. 33-38, Jan. 1990.
Uze et al., *Plasmolysis of precultured immature embryos improves Agrobacterium mediated gene transfer to rice (Oryza sativa L.)*, Plant Science, 130, pp. 87-95, 1997.
Khush (editor), *Rice Genetics III: Proceedings of the Third International Rice Genetics Symposium*, Manila, Philippines, Mar. 16-Oct. 20, 1995.
Hiei, Y. et al., *The Plant Journal*, 6(2):271-282 (1994).
Raineri, D.M. et al.., *Bio/Technology*, 8:33-38 (1990).
Chan, et al., *Plant Molecular Biology*, 22:491-506 (1993).
Aldemita, R.R., et al., *Planta*, 199:612-617 (1996).
Uze, M. et al., *Plant Science*, 130:87-95 (1997).
Zhang, J. et al., *Rice Genetics III*, 697-702 (1995).
Toki, S., *Plant Mol. Biol. Rep.*, 15:16-21 (1997)
Canadian Office Action dated Dec. 22, 2004 citing prior art in Canadian Serial. No. 2,366,104.
Dale et al., Agroinfection of Wheat: Inoculation of in Vitro Grown Seedlings and Embryos, *Plant Science*, 63 (1989, pp. 237-245.
Khanna et al., Agrobacterium-Mediated Transformation of Indicia Rice Cultivars Using Binary and Superbinary Vectors, *Aust. J. Plant Physiol.*, 1999, vol. 26, pp. 311-324.

(Continued)

Primary Examiner — Brent T Page
(74) Attorney, Agent, or Firm — Fay Sharpe LLP

(57) ABSTRACT

There is provided an *Agrobacterium* transformation method for monocotyledons, comprising a step of infecting an intact seed.

24 Claims, 3 Drawing Sheets

(56) References Cited

OTHER PUBLICATIONS

Trick et al., SAAT: Sonication-Assisted Agrobacterium-Mediated Transformation, *Transgenic Research*, 1997, vol. 6, pp. 329-336.
Encyclopedia Britannica, [Online] Retrieved from the Internet: URL:http://search.eb.com/eb/article-73122>[retrieved on May 23, 2007]; angiosperm; "Structure and function-reproductive structures-seeds".
Encyclopedia Britannica, [Online] Retrieved from the Internet: URL:http://search.eb.com/eb/article-73132>[retrieved on May 23, 2007]: angiosperm: "reproduction-seedlings".

* cited by examiner

Transformant obtained by the novel method, circa Day 50 after sowing (a)

| Conventional method | circa Day 90 after sowing | Novel method | circa Day 50 after sowing |

(b)

| Conventional method | circa Day 50 after sowing (regeneration process) | Novel method | circa Day 50 after sowing |

ULTRA-FAST TRANSFORMATION TECHNIQUE FOR MONOCOTYLEDONS

This is a continuation application of prior application Ser. No. 09/914,546 filed on Mar. 12, 2002 now abandoned, the entirety of which is incorporated herein by reference.

TECHNICAL FIELD

The present invention relates to an *Agrobacterium*-mediated transformation method for monocotyledons.

BACKGROUND ART

One means for improving a plant is a "transformation technique", in which a desired recombinant gene for modifying a character is introduced into a plant. Efficient and quick transformation techniques are extremely important for the molecular breeding of useful plants, in particular grain crops, which are important staple foods.

A majority of grain crops (e.g., rice, wheat, barley, and corn) are classified as monocotyledons. Various transformation techniques for transforming monocotyledons have hitherto been developed. Transformation techniques are generally classified into direct transformation techniques and indirect transformation techniques.

Examples of direct transformation techniques include electroporation techniques (see Shimamoto K. et al., Nature, 338: 274-276, 1989; and Rhodes C. A. et al., Science, 240:204-207, 1989), particle gun techniques (see Christou P. et al., Bio/Technology 9:957-962, 1991) and polyethylene glycol (PEG) technique (see Datta, S. K. et al., Bio/Technology, 8:736-740, 1990). Electroporation techniques and particle gun techniques have been generally used as methods for transforming monocotyledons which can achieve a relatively efficient gene introduction.

An example of an indirect transformation technique is an *Agrobacterium*-mediated transformation technique (hereinafter, this may also be referred to as an "*Agrobacterium* transformation technique"). Agrobacteria are a kind of plant pathogenic bacteria. Agrobacteria are characterized in that, when a plant is infected therewith, a T-DNA region which is present on the plasmids that Agrobacteria have (e.g., Ti plasmid or Ri plasmid) is incorporated into the plant. The *Agrobacterium* transformation technique utilizes the incorporation of the T-DNA region into plants as a means for introducing genes into plants. In short, a plant is infected with an *Agrobacterium* which contains a desired recombinant gene. After infection, a desired recombinant gene is transferred from the *Agrobacterium* into plant cells so as to be incorporated into the plant genome.

The *Agrobacterium* transformation technique is sufficiently established so far as dicotyledons are concerned. A large number of stable transformed plants have already been created which express desired recombinant genes.

On the contrary, it has conventionally been recognized as difficult to apply the *Agrobacterium* transformation technique to monocotyledons. For example, Portrykus et al. (BIO/TECHNOLOGY, 535-542, 1990) report that monocotyledons cannot be infected with Agrobacteria. On the other hand, a great deal of attempts have been made to transform monocotyledons by using Agrobacteria, which have shed light to the possibility of applying the *Agrobacterium* transformation technique to monocotyledons.

For example, Raineri et al. took the blastodisk of rice, scarred it, and placed it on a medium which induces dedifferentiation; a few days later, the blastodisk portion was infected with an *Agrobacterium*. As a result, although normally regenerated plant bodies were not obtained, calluses having a foreign gene introduced therein were successfully induced (see Raineri, D. M. et al., Bio/Technology, 8:33-38, 1990).

The pamphlet of International Publication No. WO94/00977 discloses an *Agrobacterium* transformation technique for rice and corn. According to this method, it is necessary to employ cultured tissue (e.g., calluses), which is in the process of dedifferentiation or which have completed dedifferentiation, as a plant sample to be transformed by an *Agrobacterium*. Therefore, prior to infection with an *Agrobacterium*, it takes 3 to 4 weeks to induce dedifferentiation in order to produce dedifferentiated culture tissue from a plant sample to be transformed (e.g., a leaf section).

The pamphlet of International Publication No. WO95/06722 discloses a method which infects an immature germ of rice or corn with an *Agrobacterium*. However, it is quite cumbersome to isolate immature germs.

Accordingly, it will contribute to the molecular breeding of useful monocotyledons, including grain crops such as rice, if a quicker and efficient *Agrobacterium* transformation technique for monocotyledons becomes available.

DISCLOSURE OF THE INVENTION

The present invention is intended to solve the aforementioned problems. An objective of the present invention is to improve *Agrobacterium* transformation techniques for monocotyledons. According to the method of the present invention, it is possible to create a transformed plant far more efficiently and quickly than any conventional *Agrobacterium* transformation techniques.

The present invention relates to a transformation method for monocotyledons, the method including a step of infecting an intact seed with an *Agrobacterium* which includes a desired recombinant gene. According to the method of the present invention, a seed is infected in an intact state, and no processing such as dedifferentiation of a plant sample to be transformed is required.

The seed to be infected with an *Agrobacterium* may be a seed on the fourth day to the fifth day after sowing. At the time of infection, the seed may already have germinated.

The monocotyledon to be transformed is preferably a plant of the family Gramineae, and more preferably rice (*Oryza sativa* L.).

BRIEF DESCRIPTION OF THE DRAWINGS

FIG. 3(*b*) is a photograph showing a state of living organisms, illustrating a transformed plant body obtained by a conventional technique on about the 50th day after sowing, in comparison with a transformed plant body obtained by the method according to the present invention on about the 50th day after sowing.

BEST MODES FOR CARRYING OUT THE INVENTION

Figure 1:
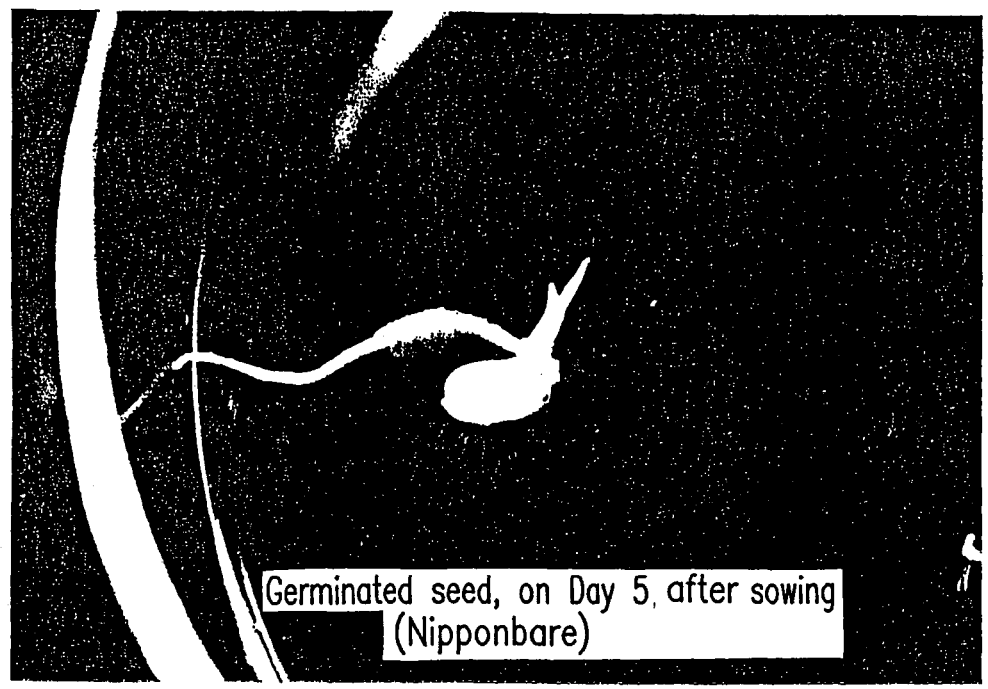
FIG. 1 is a photograph showing a state of a living organism, illustrating the state of a rice seed immediately before infection with an *Agrobacterium*.

Hereinafter, the present invention will be described in detail.

The "plants" to which the method according to the present invention is applied are monocotyledons. Examples of preferable monocotyledons include plants of the family Gramineae (e.g., rice and corn). The most preferable plant to which the method according to the present invention is applicable is rice, and in particular *Japonica* rice. Unless otherwise indicated, the term "plant" means a plant body and the seeds obtained from a plant body.

(Preparation of a Plant Expression Vector)

In order to introduce a desired recombinant gene into monocotyledons, an appropriate plant expression vector which includes the desired recombinant gene is constructed. Such a plant expression vector may be prepared by recombinant gene technologies well-known to those skilled in the art. Although pBI-type vectors are suitably employed to construct plant expression vectors for use in *Agrobacterium* transformation techniques, the plant expression vector is not limited thereto.

A "desired recombinant gene" refers to any polynucleotide which is desired to be introduced into a plant. The desired recombinant gene according to the present invention is not limited to those isolated from nature, but may also include synthetic polynucleotides. Synthetic polynucleotides may be obtained by, for example, synthesizing or modifying a gene having a known sequence by techniques well-known to those skilled in the art. The desired recombinant genes according to the present invention include, for example, any polynucleotide which is desired to be expressed in a plant to be transformed that may be endogenous or exogenous to that plant, or, in the case where it is desired to control the expression of a certain endogenous gene in a plant, a polynucleotide which includes an antisense sequence of a target gene.

In the case where expression in a plant is intended, a desired recombinant gene may contain its own promoter (i.e., the promoter to which the gene is operably linked in nature) in an operable manner, or, in the case where the gene's own promoter is not contained or where it is desirable that a promoter other than the gene's own promoter be contained, operably linked to any appropriate promoter. Examples of the promoter to be used include, a constitutive promoter, a promoter which is selectively expressed in a portion of a plant body, and an inducible promoter.

In the plant expression vector, various regulatory elements may further be linked in a such manner as to be operable within the host plant cells. The regulatory elements may include, preferably, selection marker genes, plant promoters, terminators, and enhancers. It is well-known to those skilled in the art that the type of the plant expression vector to be used and the kinds of regulatory elements may vary depending on the purpose of transformation.

A "selection marker gene" can be used in order to facilitate the selection of transformed plants. Drug resistance genes such as a hygromycin phosphotransferase(HPT) gene for imparting hygromycin resistance, and a neomycin phosphotransferase II(NPTII) gene for imparting kanamycin resistance, may be suitably employed, although not limited thereto.

A "plant promoter" means a promoter which is operably linked to a selection marker gene and expressed in a plant. Examples of such promoters include cauliflower mosaic virus (CaMV) 35S promoter and nopaline synthetase promoter, although not limited thereto.

A "terminator" is a sequence which is located downstream of a region of a gene which codes for a protein, and which is involved in the termination of transcription when DNA is transcribed to mRNA, as well as the addition of a polyA sequence. Examples of terminators include CaMV35S terminator and the nopaline synthetase terminator (Tnos), although not limited thereto.

An "enhancer" may be employed in order to enhance the expression efficiency of a target gene. As the enhancer, an enhancer region which includes an upstream sequence within the CaMV35S promoter is suitably used. A plurality of enhancers may be employed for each plant expression vector.

(Transformation of Plants)

The *Agrobacterium* used for the transformation of monocotyledons may be any bacterium of the genus *Agrobacterium*, and preferably *Agrobacterium tumefaciens*. The *Agrobacterium* may be transformed by a plant expression vector containing a desired recombinant gene (e.g., by electroporation). By infecting a seed with the transformed *Agrobacterium*, the desired recombinant gene can be introduced into the plant. The introduced recombinant gene exists in a form integrated within the genome in the plant. The genome in the plant not only means chromosomes in the nucleus, but also includes genome included in various organelles (e.g., mitochondria, chloroplasts) in plant cells.

After removing the husks of the seed of a plant which is intended to be transformed, the seed is pre-cultured in an intact state. A seed being "intact" means that the seed has not been subjected to any artificial manipulations, such as removal of the ovule or scarring of the blastodisk.

In the pre-culture, the seeds are sown on a medium (e.g., an N6D medium) containing an appropriate concentration of auxin (e.g., 2,4-D), and may be incubated for typically 4 to 5 days, and preferably 5 days. The pre-culture is completed before the seed tissue enters into a dedifferentiation process. The temperature during the pre-culture is typically 25° C. to 35° C., and preferably 27° C. to 32° C. After completing the pre-culture, the seeds are sterilized, and thereafter washed well with water. Next, the seeds may be infected with a transformed *Agrobacterium* under aseptic manipulation.

During infection by the *Agrobacterium* (co-culture), the seeds are incubated in the dark, typically for 2 to 5 days, and preferably for 3 days. The temperature at this time is typically 26° C. to 28° C., and preferably 28° C. Next, in order to eliminate the *Agrobacterium* in the medium, the seeds are subjected to a treatment with an appropriate bacteria eliminating agent (e.g., carbenicillin). The transformed seeds are selected on the basis of a selection marker (e.g., drug resistance such as hygromycin resistance).

After the culture under appropriate bacteria-eliminating conditions and selection conditions, the selected transformed seeds may be placed in a regeneration medium (e.g., an MS medium) containing appropriate plant regulatory substances, and incubated for an appropriate period of time. In order to allow a plant body to be regenerated, the regenerated transformant is placed on a rooting medium (e.g., an MS medium containing no plant regulatory substances). After the growth of roots is confirmed, the transformant may be potted.

The desired recombinant gene which has been introduced into the plant may have action for intended purposes (e.g., expression of a new character of interest, or controlling the expression of certain endogenous genes) within the plant.

It can be confirmed by using well-known techniques whether or not a desired recombinant gene has been introduced into a plant. This confirmation may be made, for example, via Northern Blot analysis. Specifically, the entire RNA is extracted from a leaf of a regenerated plant, subjected to electrophoresis on agarose in de-natured condition, and thereafter blotted on an appropriate membrane. By allowing a labeled RNA probe which is complementary to a portion of the introduced gene to hybridize with the blots, the mRNA of the gene of interest can be detected. Alternatively, in the case where controlling the expression of an endogenous gene in the plant is desired via the introduction of a desired recombinant gene, the expression of the target endogenous gene may be tested for example, via the aforementioned Northern Blot analysis. If the expression of the target endogenous gene is significantly suppressed as compared to its expression in a non-transformed control plant, it is confirmed that the desired recombinant gene has been introduced into the plant and that the desired recombinant gene has acted to control the expression.

Conventional methods usually require a period of 3 to 4 weeks for inducing dedifferentiation prior to *Agrobacterium* infection. In contrast, the method according to the present invention does not require a step of inducing dedifferentiation, so that the number of days required for creating transformation monocotyledons can be reduced. Furthermore, according to the method of the present invention, it is also possible to reduce the period which is required for selection by conventional techniques, so that it is possible to reduce the influences of culture variation.

In a preferable embodiment of the method according to the present invention, the number of days required for creating a transformation monocotyledon is about 50 days, which is about two-thirds or less of the number of days (about 90 days) required by conventional *Agrobacterium* transformation methods (see, for example, Example 2 below). Moreover, according to the method of the present invention, a transformation efficiency of 10% to 15% can be obtained in the case of *Nipponbare* seeds. A similarly high transformation efficiency can also be achieved with other rice cultivars such as *Dontokoi* or *Kitaake*. Therefore, by using the method according to the present invention, it is possible to more efficiently and quickly create a transformed plant than by conventional transformation techniques.

EXAMPLES

Hereinafter, the present invention will be specifically described with respect to examples, which do not limit the present invention. The materials, reagents, and the like which are used in the example are available from commercial sources unless otherwise specified.

Example 1

Transformation of a Rice Plant Using the Method According to the Present Invention After removing the husks of the seeds of Nipponbare, a typical rice cultivar, the seeds in an intact state were sterilized in a 2.5% sodium hypochlorite (NaClO) solution. After being washed well with water, the rice was subjected to the following aseptic manipulations.

1.1 Pre-Culture

The seeds were sown on an N6D medium containing 2,4-D (30 g/l of sucrose, 0.3 g/l of casamino acid, 2.8 g/l of proline, 2 mg/l of 2,4-D, 4 g/l of gellite, pH5.8), and incubated at 27° C. to 32° C. for 5 days. The seeds germinated during this period (FIG. 1).

1.2 Plant Expression Vector

As a plant expression vector for transforming an *Agrobacterium*, a plasmid pIG121Hm, in which the GUS gene including a first intron of the *Ricinus catalase* gene and a hygromycin resistance gene are linked, was used (Nakamura et al., PLANT BIOTECHNOLOGY II, a special issue of Gendai Kagaku, pp. 123-132 (1991)). *Agrobacterium* EHA101 was transformed with pIG121Hm (Hood et al., J. Bacteriol., 168: 1291-1301(1986)). EHA101 is a bacterium in which a vir region of a helper plasmid is derived from the strongly pathogenic *Agrobacterium* A281.

1.3 *Agrobacterium* Infection

In a suspension of the transformed *Agrobacterium*, the aforementioned pre-cultured seeds were immersed. Thereafter, this was placed on a 2N6-AS medium (30 g/l of sucrose, 10 g/l of glucose, 0.3 g/l of casamino acid, 2 mg/l of 2,4-D, 10 mg/l of acetosyringon, 4 g/l gellite, pH5.2). This was incubated in the dark at 28° C. for 3 days to effect co-culturing.

1.4 Bacterium Elimination and Selection

After completing the co-culture, an N6D medium containing 500 mg/l of carbenicillin, the *Agrobacterium* was washed off the seeds. Next, the selection of the transformed seeds was performed under the following conditions.

First selection: the seeds were placed on an N6D medium containing 2 mg/l of 2,4-D which was supplemented with carbenicillin (500 m g/l) and hygromycin (25 mg/l), and incubated at 27° C. to 32° C. for 7 days.

Second selection: the seeds were placed on an N6D medium containing 2 to 4 mg/l of 2,4-D which was supplemented with carbenicillin (500 m g/l) and hygromycin (25 mg/l), and incubated at 27° C. to 32° C. for 7 more days.

1.5 Regeneration

The selected transformed seeds were allowed to regeneration under the following conditions.

First regeneration: the selected seeds were placed on a redifferentiation medium (an MS medium (30 g/l of sucrose, 30 g/l of sorbitol, 2 g/l of casamino acid, 2 m g/l kinetin, 0.002 mg/l NAA, 4 g/l gellite, pH5.8) supplemented with carbenicillin (500 mg/l) and hygromycin (25 m g/l)), and incubated at 27° C. to 32° C. for 2 weeks.

Second regeneration: by employing the same regeneration medium as that used for the first regeneration, an incubation was performed at 27° C. to 32° C. for 2 more weeks.

1.6 Potting

Figure 2:
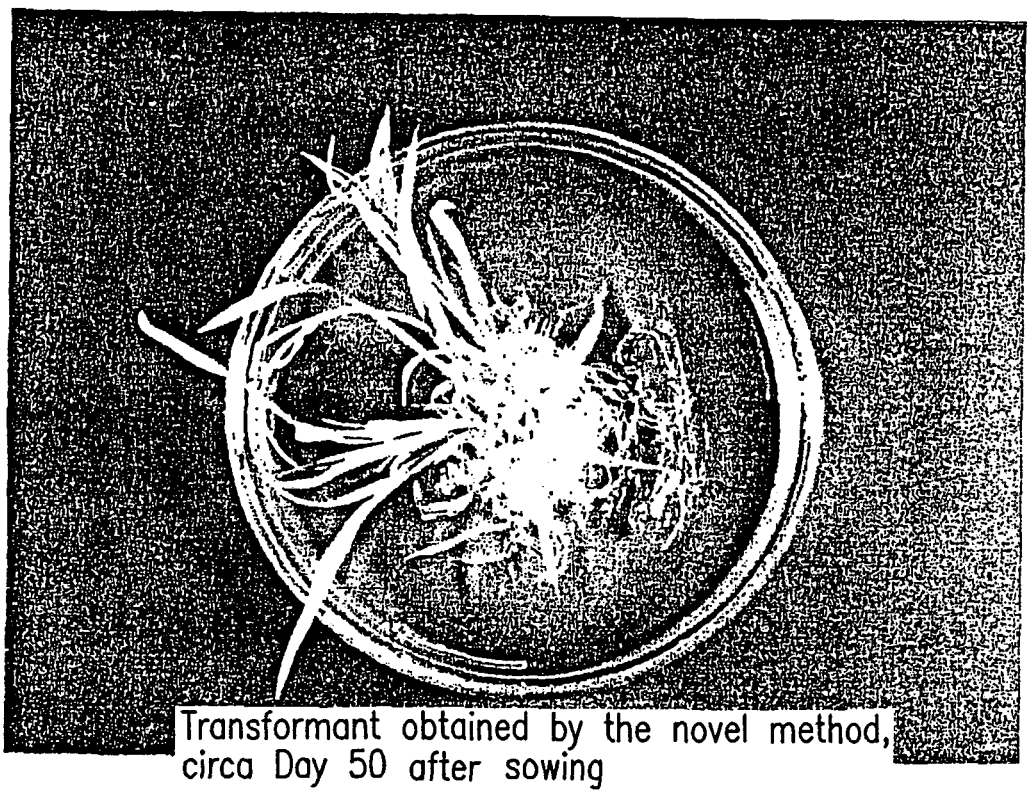
FIG. 2 is a photograph showing a state of a living organism, illustrating a regenerated rice individual obtained by the method according to the present invention, on about the 50th day after sowing.

The transformants which had regenerated were placed on a rooting medium (an MS medium containing no hormones, supplemented with hygromycin (25 m g/l). After the growth of roots was confirmed, the transformants were potted (FIG. 2).

Example 2

Transformation of a Rice Plant Using a Conventional Method

For comparison with the method described in Example 1, a rice plant transformation according to a conventional method was performed as follows, using Nipponbare as the material to be transformed.

2.1 Callus Induction

After removing the husks of the seeds of Nipponbare, the seeds were sterilized and sown on a callus induction medium (an N6D medium containing 2 m g/l of 2,4-D), and incubated at 30° C. under light. About 4 weeks after the beginning of callus induction, the grown calluses derived from blastodisks were used for transformation.

2.2 Transformation

The resultant calluses were infected with *Agrobacterium* EHA101 which was transformed with a plant expression vector pIG121Hm as described in Example 1, and incubated on an 2N6-AS medium in the dark at 28° C. for 3 days to effect co-culturing.

2.3 Bacterium Elimination and Selection

By using an N6D medium containing 500 m g/l of carbenicillin, the *Agrobacterium* was washed off the calluses. Next, the selection of the transformed callus was performed under the following conditions.

First selection: the calluses were placed on an N6D medium containing 2 mg/l of 2,4-D which was supplemented with carbenicillin (500 mg/l) and hygromycin (50 mg/l), and incubated at 27° C. to 32° C. for 2 weeks.

Second selection: the calluses were placed on an N6D medium containing 2 to 4 mg/l of 2,4-D which was supplemented with carbenicillin (500 m g/l) and hygromycin (50 mg/l), and incubated at 27° C. to 32° C. for 2 more weeks.

2.4 Regeneration, Rooting and Potting

The selected transformed seeds were allowed to regeneration under similar conditions to those employed in Example 1, and all the processes down to potting were carried out.

2.5 Results

Figure 3:
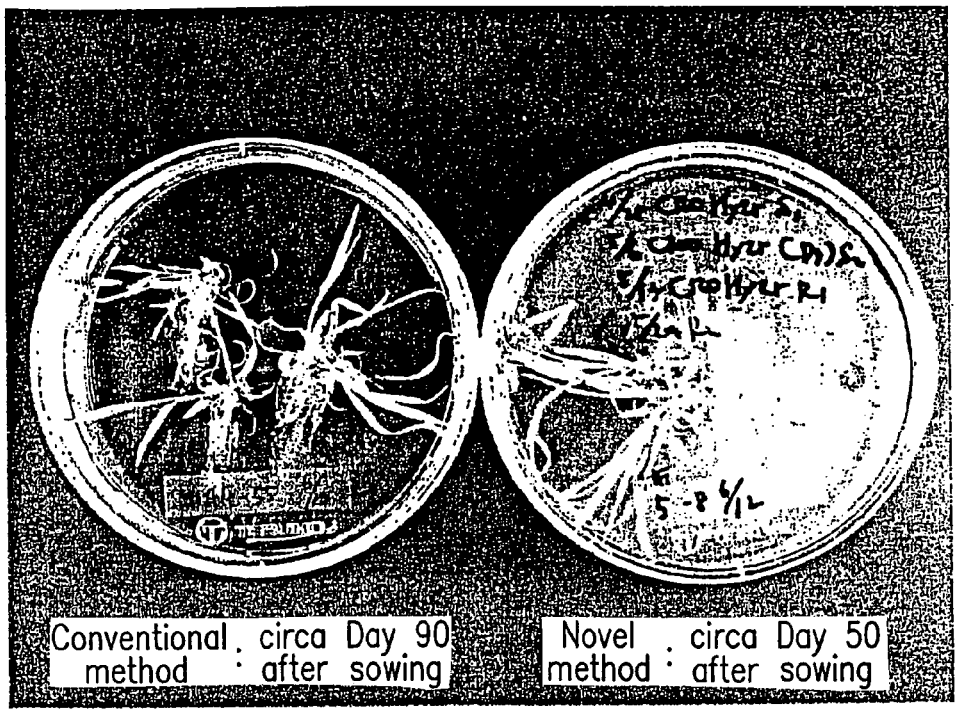
FIG. 3(*a*) is a photograph showing a state of living organisms, illustrating a transformed plant body obtained by a conventional technique on about the 90th day after sowing, in comparison with a transformed plant body obtained by the method according to the present invention on about the 50th day since sowing.
Figure 3:

FIG. 3 comparatively illustrates a transformation example according to a conventional method, and a transformation example according to the method of the present invention. The number of days which were required after sowing until the potting of the transformants was about 90 days for the conventional technique, as opposed to about 50 days for the method according to the present invention (FIG. 3 (*a*)). A comparison on about the 50th day since sowing indicated that, while the transformants obtained according to the method of the present invention were ready to be potted, transformants obtained according to the conventional method were still in the process of regeneration (FIG. 3 (*b*)). In summary, the method according to the present invention reduced the period required for transformation to about two-thirds or less of that required by the conventional method.

INDUSTRIAL APPLICABILITY

According to the present invention, an improved *Agrobacterium*-mediated transformation method for monocotyledons is provided. According to the method of the present invention, intact seeds of a plant which is intended to be transformed are infected with an *Agrobacterium* which contains a desired recombinant gene. The use of the present invention enables a more efficient and quicker creation of a transformed plant.

The invention claimed is:

1. A method for obtaining at least one transformed rice plant having roots and leaves in 50 days or less comprising:
    pre-culturing intact rice seeds on a medium containing an auxin for 4 to 5 days to obtain precultured rice seeds;
    wherein the pre-culturing step is completed before the seeds dedifferentiate, wherein the pre-cultured seeds are seeds or germinated seeds;
    infecting the precultured intact rice seeds with *Agrobacterium* containing a recombinant DNA of interest and incubating the seeds for 2 to 5 days in the dark to obtain infected rice seeds;
    selecting for seeds containing the DNA of interest by placing, for 14 days, the infected rice seeds on a medium containing a substance which selects for seeds containing the DNA of interest; and
    regenerating the selected seeds to obtain at least one transformed rice plant having roots and leaves.

2. A method for obtaining at least one transformed rice plant having roots and leaves in 50 days or less comprising:
    pre-culturing intact rice seeds on a medium containing an auxin for 5 days to obtain precultured rice seeds;
    wherein the pre-culturing step is completed before the seeds dedifferentiate, wherein the pre-cultured seeds are seeds or germinated seeds;
    infecting the precultured intact rice seeds with *Agrobacterium* containing a recombinant DNA of interest and incubating the seeds for 3 days in the dark to obtain infected rice seeds;
    selecting for seeds containing the DNA of interest by placing, for 14 days, the infected rice seeds on a medium containing a substance which selects for seeds containing the DNA of interest; and
    regenerating the selected seeds for 28 days to obtain at least one transformed rice plant having roots and leaves.

3. A method for obtaining at least one transformed rice plant having roots in 50 days or less consisting of:
    pre-culturing intact rice seeds on a medium containing 2 mg/L 2,4-D for 5 days at a temperature of from about 27° C. to about 32° C. to obtain precultured rice seeds;
    wherein the pre-culturing step is completed before the seeds dedifferentiate, wherein the pre-cultured seeds are seeds or germinated seeds;
    infecting the precultured intact rice seeds by immersing the precultured seeds in a suspension of *Agrobacterium* containing a recombinant DNA of interest, incubating the seeds in the dark at a temperature of about 28° C. for 3 days, and eliminating the *Agrobacterium* using carbenicillin;
    selecting for seeds containing the DNA of interest a first instance by placing the seeds on a medium containing 2,4-D, carbenicillin, and hygromycin and incubating at a temperature of from about 27° C. to about 32° C. for 7 days,
    selecting for seeds containing the DNA of interest a second instance by placing the seeds on a medium containing 2,4-D, carbenicillin, and hygromycin, and incubating at a temperature of from about 27° C. to about 32° C. for 7 days; and
    regenerating the selected seeds using a regeneration medium for 28 days at a temperature of from about 27° C. to about 32° C. to obtain at least one transformed rice plant having roots.

4. A method according to claim 2, wherein the pre-cultured seeds are germinated seeds.

5. A method according to claim 3, wherein the pre-cultured seeds are germinated seeds.

6. A method according to claim 2, wherein the medium further contains a nutrient.

7. A method according to claim 3, wherein the medium further contains a nutrient.

8. A method according to claim 2, wherein the medium further contains sucrose.

9. A method according to claim 3, wherein the medium further contains sucrose.

10. A method according to claim 2, wherein the DNA of interest further comprises a drug resistance gene.

11. A method according to claim 3, wherein the DNA of interest further comprises a drug resistance gene.

12. A method according to claim 2, wherein the medium further contains a bacteria eliminating agent.

13. A method according to claim 3, wherein the medium further contains a bacteria eliminating agent.

14. A method according to claim 2, wherein the step of allowing the selected seeds to produce at least one transformed rice plant is conducted by regenerating plants using regeneration medium containing a hormone.

15. A method according to claim 3, wherein the step of allowing the selected seeds to produce at least one transformed rice plant is conducted by regenerating plants using regeneration medium containing a hormone.

16. A method according to claim 2, wherein the *Agrobacterium* is *Agrobacterium tumefaciens*.

17. A method according to claim 3, wherein the *Agrobacterium* is *Agrobacterium tumefaciens*.

18. A method according to claim 1, wherein the pre-cultured seeds are germinated seeds.

19. A method according to claim 1, wherein the medium further contains a nutrient.

20. A method according to claim 1, wherein the medium further contains sucrose.

21. A method according to claim 1, wherein the DNA of interest further comprises a drug resistance gene.

22. A method according to claim 1, wherein the medium further contains a bacteria eliminating agent.

23. A method according to claim 1, wherein the step of allowing the selected seeds to produce at least one transformed rice plant is conducted by regenerating plants using regeneration medium containing a hormone.

24. A method according to claim 1, wherein the *Agrobacterium* is *Agrobacterium tumefaciens*.

\* \* \* \* \*